(12) United States Patent
Goswami et al.

(10) Patent No.: US 6,428,823 B1
(45) Date of Patent: Aug. 6, 2002

(54) BIOLOGICALLY ACTIVE AQUEOUS FRACTION OF AN EXTRACT OBTAINED FROM A MANGROVE PLANT *SALVADORA PERSICA* L

(75) Inventors: Usha Goswami; Nazarine Fernandes, both of Goa (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/818,562

(22) Filed: Mar. 28, 2001

(51) Int. Cl.[7] ................................................ A61K 35/78
(52) U.S. Cl. ........................ 424/769; 514/935; 424/725
(58) Field of Search .................................. 424/769, 725; 514/935

(56) References Cited

U.S. PATENT DOCUMENTS

| | | |
|---|---|---|
| 5,190,979 A | 3/1993 | Herman |
| 5,607,741 A | 3/1997 | Zimmerman et al. |
| 5,804,206 A | 9/1998 | D'Amelio et al. |
| 5,804,575 A | 9/1998 | Pezzuto et al. |
| 5,910,307 A | 6/1999 | Kwak et al. |
| 5,948,460 A | 9/1999 | Kang et al. |
| 5,962,527 A | 10/1999 | Pezzuto et al. |
| 6,048,847 A | 4/2000 | Ramadoss et al. |

OTHER PUBLICATIONS

F. Nazarine, et al., "Pharmacological activities of extracts of some marine animals and plants on isolated tissues of the guinea–pig", Indian J.Mar. Sci., vol. 27, pp. 499–501, Sep. and Dec. 1998.

Emily Pisha, et al., "Discovery of betulinic acid as a selective inhibitor of human melanoma that functions by induction of apoptosis", Nature Medicine, vol. 1, No. 10, pp. 1046–1051, Oct. 1995.

Toshihiro Fujioka, et al., "Anti–Aids Agents, 11. [1]Betulinic Acid and Platanic Acid as Anti–HIV Principles from *Syzigium claviflorum*, and the Anti–HIV Activity of Structurally Related Triterpenoids", Journal of Natural Products, vol. 57, No. 2, pp. 243–247, Feb. 1994.

*Primary Examiner*—Christopher R. Tate
*Assistant Examiner*—Randall Winston
(74) *Attorney, Agent, or Firm*—Piper Rudnick LLP; Wilburn L. Chesser

(57) ABSTRACT

The invention discloses a process of extracting, fractionating and purifying bioactive molecules from an associated mangrove plant, methods of screening for pharmacological activities of crude extract, it fractions and purified compounds and the use of the aqueous fraction of the crude extract as a tocolytic agent.

6 Claims, 5 Drawing Sheets

Figure 1A:

(1 of 5 Drawing Sheet(s) Filed in Color)

β-AMYRIN

BETULIN

URSOLIC ACID

METHYL PALMITATE

LUPEOL

BIOLOGICALLY ACTIVE AQUEOUS FRACTION OF AN EXTRACT OBTAINED FROM A MANGROVE PLANT *SALVADORA PERSICA* L

FIELD OF THE INVENTION

The invention relates to biologically active extracts obtained from the plant *Salvadora persica* Linneaus 1753. The invention also provides a process for obtaining the crude extract. Further the invention provides pharmaceutical compositions, exhibiting biological activity, especially tocolytic activity.

PRIOR ART REFERENCES

The associated mangrove plant, *Salvadora persica* Linneaus, 1753, belongs to the order Salvadoracea and are shrubs or small trees with white flowers frequent in degraded mangrove swamps and saline banks all over the west coast of India. Large numbers of marine plants have been examined for bioactive substances. Nazarine, F; Anita F; Rataboli, P. V.; Diniz D'Souza, R. S and Dhume; V. G., 1998 in Indian Journal of marine Sciences, 27: 499–501 have reported promising pharmacological activities in marine organisms from Indian waters.

There are several patents available from all over the world related to processes and compounds from nature for various purposes. Kwak; Wie-jong; Han; Chang-kyun; kum; Hwan-su; An; Jae-suk; Kum; Taek-soo, patented process of extracting and purifying biologically effective ingredients from combined medicinal plant and their extract composition (U.S. Pat. No. 5,910,307 published on Jun. 8, 1999). D'Amelio; Frank S; Mirhom; Youssef W. disclosed therapeutic composition and method for treating skin using extract from *Centipeda cunninghami* plant in U.S. Pat. No. 5,804,206 published on Sep. 8, 1998. Zimmerman; Richard C.; Alber; Randall S.; Todd; James S.; Crews; Philip, isolated compound from the methanolic extract of the eelgrass *Zostrea marina* having significant antifouling aquatic properties (U.S. Pat. No. 5,607,741 published on Mar. 4, 1997).

Betulinic acid which is prepared from the compound Betulin has many pharmaceutical potentials. Pezzuto John M; Kim; Darrick S. H. L. disclosed methods of manufacturing betulinic acid from betulin (U.S. Pat. No. 5,804,575 published on Sep. 8, 1998). The betulinic acid is intensively investigated as a potential therapeutic agent for a variety of diseases. Pezzuto; John, M; Das Gupta, Tapas K; Schmidt; Mary Lou; Kuzmanoff; Konrad Marc; Ling Indeck; Lydia and Kim; Darrick, S. H. L. (U.S. Pat. No. 5,962,527 dated Oct. 5, 1999). Pisha E, Chai H, Lee I S, Chagwedera T E, Framsworth N R, Cordell G A, Beecher C W, Fong H H, Kinghom A D, Brown D M, in Nature medicine, 1 pages 1046–1051 (1995) discloses that betulinic acid has an unexpected selective anti-tumour activity against human melanoma e.g. MEL-1, MEL-2 and MEL-4. In addition Fujioka T, Kashiwada Y, Kilkuskie R E, Cosentino L M, Ballas L M, Jiang J B, Janzen W P, Chen I S, Lee K H. J.Nat.Prod., 57 (2) pages 243–247 (1994) discloses that betulinic acid has anti-HIV activity in H9 lymphocytic cells. These inventors mentioned that the researches directed t betulinic acid as therapeutic agent are hindered because the betulinic acid is available in very limited quantities and at a very high cost. Ramadoss, Sunder, Jaggi, Manu; Siddiqui; Mohammad Jamshed Ahmed in U.S. Pat. No. 6,048,847 published on Apr. 11, 2000 describes uses of betulinic acid and its derivatives for inhibiting cancer growth and a method of monitoring this Kang; Raphael K. L.; Zyzak; Li Li; nakatsu; Tetsuo published flavoured product additives in U.S. Pat. No. 5,948,460, dated Sep. 7, 1999 in which Ursolic acid was one of the compound amongst a group of three compounds which was added to a flavoured product to reduce aftertaste in the product and enhance its sweetness like in a diet drink. It was also used as a constituent in a preparation for inhibition of skin Tumorigenesis.

Herman, S (U.S. Pat. No. 5,190,979 published on Mar. 2, 1993) disclosed lupeol also as a compound which can make pharmacologically active terpene ozonides which have medicinal value.

OBJECTS OF THE INVENTION

The main object of the present invention is to provide a process for obtaining a crude extract from stem, leaves, and flowers of *Salvadora persica*, a commonly available shrub in mangrove swamps and screening to study its bioactivity.

Another object of the invention is to isolate naturally occurring compounds from the plant *Salvadora persica* and identify their molecular weights, molecular formulae, melting points and their structural formulae, which will be helpful in chemical synthesis of these compounds.

Yet another object of the invention is pharmacological screening of crude extract, its fractions and purified compounds to check that the activities shown by the crude extract and fractions is maintained throughout.

Another object of the invention is to provide pharmaceutical compositions containing extracts from the plant *Salvadora persica* and exhibiting biological activity, especially, tocolytic activity.

SUMMARY OF THE INVENTION

The present invention seeks to overcome the drawbacks inherent in the prior art by providing the highly efficient and selective means for processing of active crude extract its fractionation, isolation and purification of the active compounds. Further the invention provides pharmaceutical compositions containing the extract obtained from the plant *Salvadora persica* and useful in relieving pains in the uterine muscles.

DETAILED DESCRIPTION OF THE INVENTION

The present invention discloses for the first time the methods of isolation, purification and pharmacological screening of all these above said commercially important compounds from a commonly available plant from mangrove swamps of the west coast of India. The said plant identified as *Salvadora persica*, is an associated mangrove plant. It is a shrub and the twigs with leaves of flowers can be hand picked. Even the crude extract and fractions exhibit therapeutic value. The important point is that the biological activity shown by the extract is maintained in the purified compounds such as Methyl palmitate and Betulin.

This disclosure points towards future potential clinical uses of the extract and fractions for treatment of diseases such as smooth muscle relaxant, bronchial asthma, renal colics and prevention of premature delivery. It further relates to the use of Methyl palmitate and Betulin in motion sickness, abdominal cramps.

The invention provides methods whereby biologically active crude extract of an associated mangrove plant identified as *Salvadora persica* Linneaus 1753 is prepared. *Salvadora persica* Linneaus (Salvadoraceae) are shrubs or small trees with white flowers frequent in degraded mangrove swamps and saline banks all over the west coast of India; west Asia. The process disclosed in the invention further relates to the extraction, fractionation and purification of active constituent metabolites of the said plant. The invention is also concerned with the spectral identification of the compounds such as β-amyinn (non-steroidalpolycyclic triterpene), Betulin, Ursolic acid (triterpenic acid), Methyl palmitate (A liphatic Ester) and Lupeol (non-steroidalpolycylic triterpene). The invention also deals with molecular formulae, molecular weights, melting points and structural formulae of the said compounds. The invention provides a highly efficient and selective means for processing of active crude extract obtained from *Salvadora persica*, its fractionation, isolation and purification. As used herein, the terms fractionation means separating the crude extract. The term isolation and fractionation means separating the fraction into pure compounds.

The invention further relates to methods of screening pharmacological activities of the said compounds in mammalian tissues. The applicant has found that the crude extract obtained from the plant *Salvadora persica* can be separated into two fractions, i.e., chloroform and aqueous fractions. The aqueous fraction was found to exhibit tocolytic activity, which is described in detail in the present invention.

Accordingly, the invention provides a process of extracting and purifying biologically useful molecules from an associated mangrove plant which comprises the steps of:
 i) collecting and processing the plant plants of *Salvadora persica*,
 ii) preparing a crude extract from the plant parts of *Salvadora persica*,
 iii) testing the crude extract using methods of pharmacology,
 iv) fractionating the crude extract,
 v) testing the fractions using methods of pharmacology,
 vi) isolating the pure compounds by column chromatography,
 vii) testing the pure compounds by using methods of pharmacology, and
 viii) identifying the compounds by spectroscopy.

As said earlier, the aqueous fraction of the crude extract obtained from the mangrove plant *Salvadora persica* showed tocolytic activity, while the remaining 2 fractions (butanol and petroleum ether) were inactive.

The invention also provides the identification of the molecules from the spectral data. The molecular formulae of the five compounds is provided from the spectral data. The invention provides molecular weights of the molecules from EIMS. The structural formulae of the compounds is also provided from the spectral data.

Thus, a crude extract was obtained from the plant *Salvadora persica*. The crude extract was tested for its bioactivity and if found promising in terms of its pharmacological activity, it was fractionated using solvents with increasing polarity to obtain fractions such as petroleum ether, chloroform, butanol and aqueous. Each of these were also tested for their pharmacological activity.

The five compounds purified from the extract of the plant were β-amyrin (non-steroidalpolycyclic triterpene), Betulin, Ursolic acid (triterpenic acid), Methyl palmitate (Aliphatic Ester) and Lupeol (non-steroidalpolycyclic triterpene).

β-amyrin was found to be a non-steroidalpolycyclic triterpene with the following details:

| Molecular formula | : $C_{30}H_{50}O$ |
|---|---|
| Molecular weight | : 426 |
| Melting point | : 160.degree. C. |

Another molecule found was betulin having:

| Molecular formula | : $C_{30}H_{50}O_2$ |
|---|---|
| Molecular weight | : 442 |
| Melting point | : 255 degree. C. |

Ursolic acid (triterpenic acid) molecule was also found in the extract. It had:

| Molecular formula | : $C_{30}H_{48}O_3$ |
|---|---|
| Molecular weight | : 456 |
| Melting point | : 292 degree. C. |

Methyl palmitate (Aliphatic Ester) found in the extract had:

| Molecular formula | : $C_{16}H_{32}O_2$ |
|---|---|
| Molecular weight | : 256 |
| Melting point | : 30 degree. C. |

Lupeol (non-steroidalpolycyclic triterpene) found in the extract had:

| Molecular formula | : $C_{30}H_{50}O$ |
|---|---|
| Molecular weight | : 426 |
| Melting point | : 215 degree. C. |

One of the compounds Betulin which can be used in manufacturing of betulinic acid (U.S. Pat. No. 5,804,575 published on Sep. 8, 1998. Betulinic acid is intensively investigated as a potential therapeutic agent for a variety of diseases.

Ursolic acid is added to a flavoured product to reduce aftertaste in the product and enhance its sweetness for example in a diet drink. It was also used as a constituent in a preparation for inhibition of skin Tumorigenesis.

Extracts of some plants show vasoconstrictor and analgesic properties and also contain triterpenoid beta.-amyrin. These compositions for inhibiting the formation of unwanted skin pigmentation combine high tyrosinase blocking capabilities with stability in cosmetic preparations, absence of significant cytotoxic effects and synergy of action (U.S. Pat. Nos. 5,773,014, 5,679,393). Beta.-amyrin and lupeol are used as components for dimethylsterols in medical formulations (U.S. Pat. No. 4,808,574).

Methyl palmitate is compound used in making alcohols as mentioned in U.S. Pat. No. 6,049,013 published on April, 2000. Lupeol can be used as a component for several remedial medicines, insect repellants, distilleries anti tumour and chemical industries (U.S. Pat. Nos. 4,808,574; 5,962,527; 5,908,628).

Thus, the extract of *Salvadora persica* contained several compounds as listed above. The aqueous fraction of the extract of the said plant *Salvadora persica*, was then tested for its biological activity on guinea pigs. The Applicants, to their surprise found that the aqueous fraction exhibited excellent tocolytic activity.

Accordingly, the invention provides compositions containing the aqueous fraction of the extract obtained from *Salvadora persica*, optionally with conventional additives for relieving pains in the uterine muscles. The composition may contain about 10 μgm of the extract. Thus, the aqueous fraction of the crude extract obtained from the plant *Salvadora persica* is a potential tocolytic agent. The compositions may be formulated in different physical forms, as may be required. The extract may be used as such or with conventional additives, physiologically acceptable carriers, preservatives, buffers, etc. as required.

Additionally, the invention provides a method of treating tocolytic conditions, which comprises administration of therapeutically effective amount of extract obtained from *Salvadora persica* to the subject in need thereof. The extract may be administered at a dosage level in the range of 50 μg/ml to 250 μg/ml, in case of normal adults. The exact dosage will vary depending on the patient to be treated and will depend on factors such as requirements of the patient, severity of the condition being treated and the activity of the extract. The determination of optimum dosages for a particular patient is well-known to those skilled in the art.

DETAILED DESCRIPTION OF THE ACCOMPANYING DRAWINGS

The file of this patent contains at least one drawing executed in color. Copies of this patent with color drawings will be provided by the Patent and Trademark Office upon request and payment of the necessary fee.

Figure 1B:

FIG. 1(*a*) shows the mangrove plant and

FIG. 1(*b*) shows the twig of the associated mangrove plant used.

Figure 2:
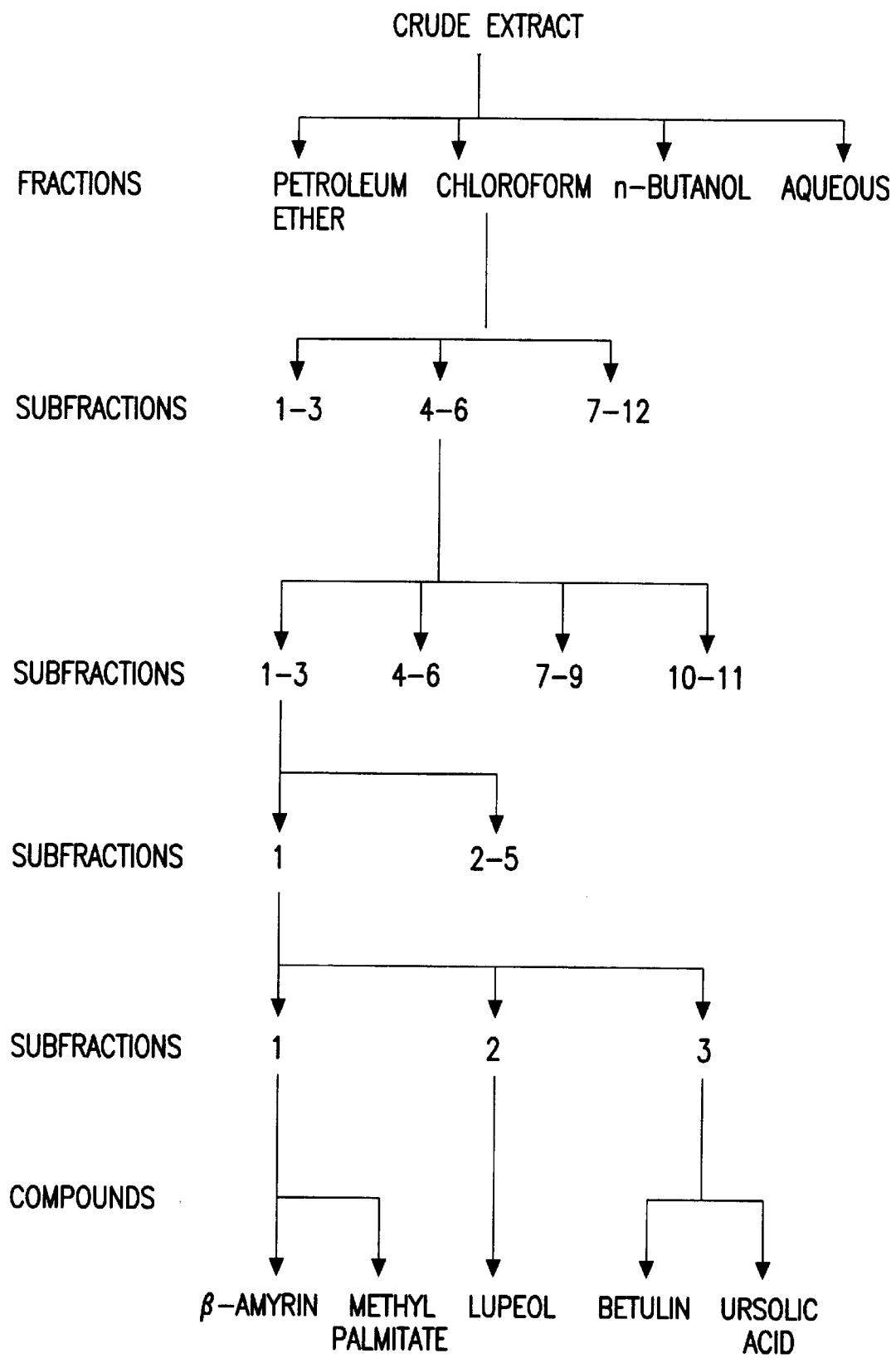

FIG. 2: shows the different fractions obtained from the crude extract of the plant *Salvadora persica*.

Figure 3:
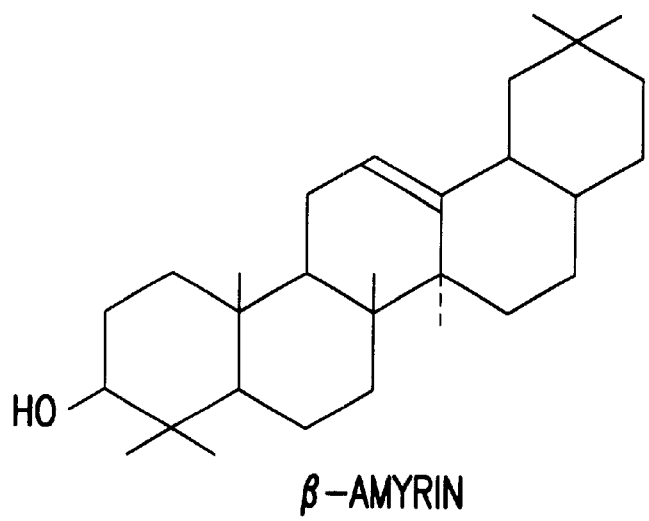

FIG. 3: shows the structural formula of β-amyrin ( non-steroidalpolycyclic triterpene)

Figure 4:
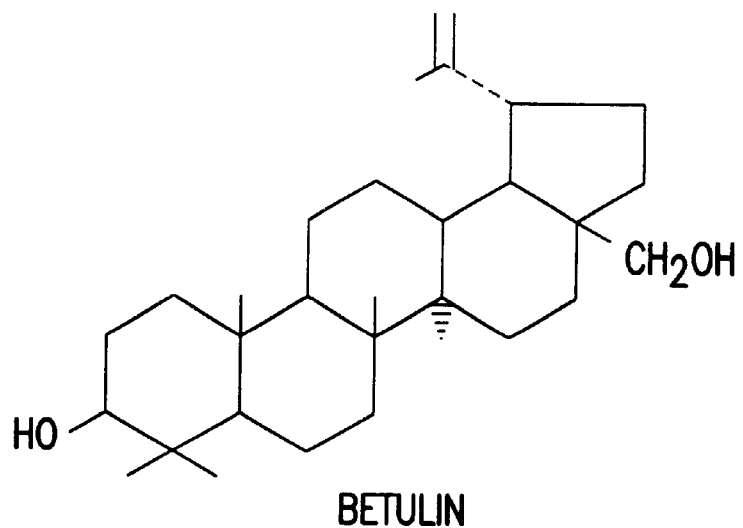
Figure 5:
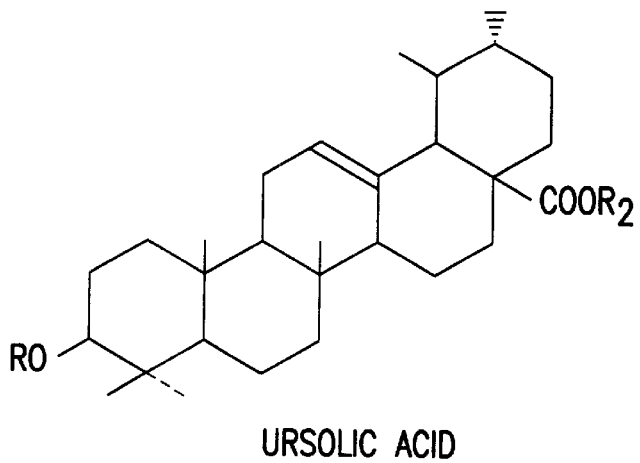
Figure 6:
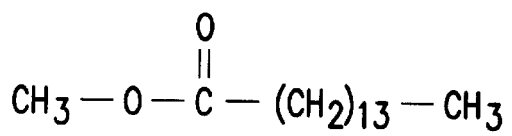

FIG. 4: Structural formula of Betulin,

FIG. 5: Structural formula of Ursolic acid (triterpenic acid),

FIG. 6: Structural formula of Methyl palmitate (Aliphatic Ester)

Figure 7:
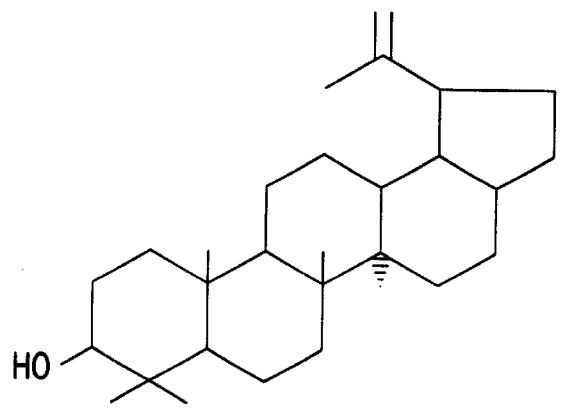

FIG. 7: Structural formula of Lupeol (non-steroidalpolycyclic triterpene).

Figure 8:
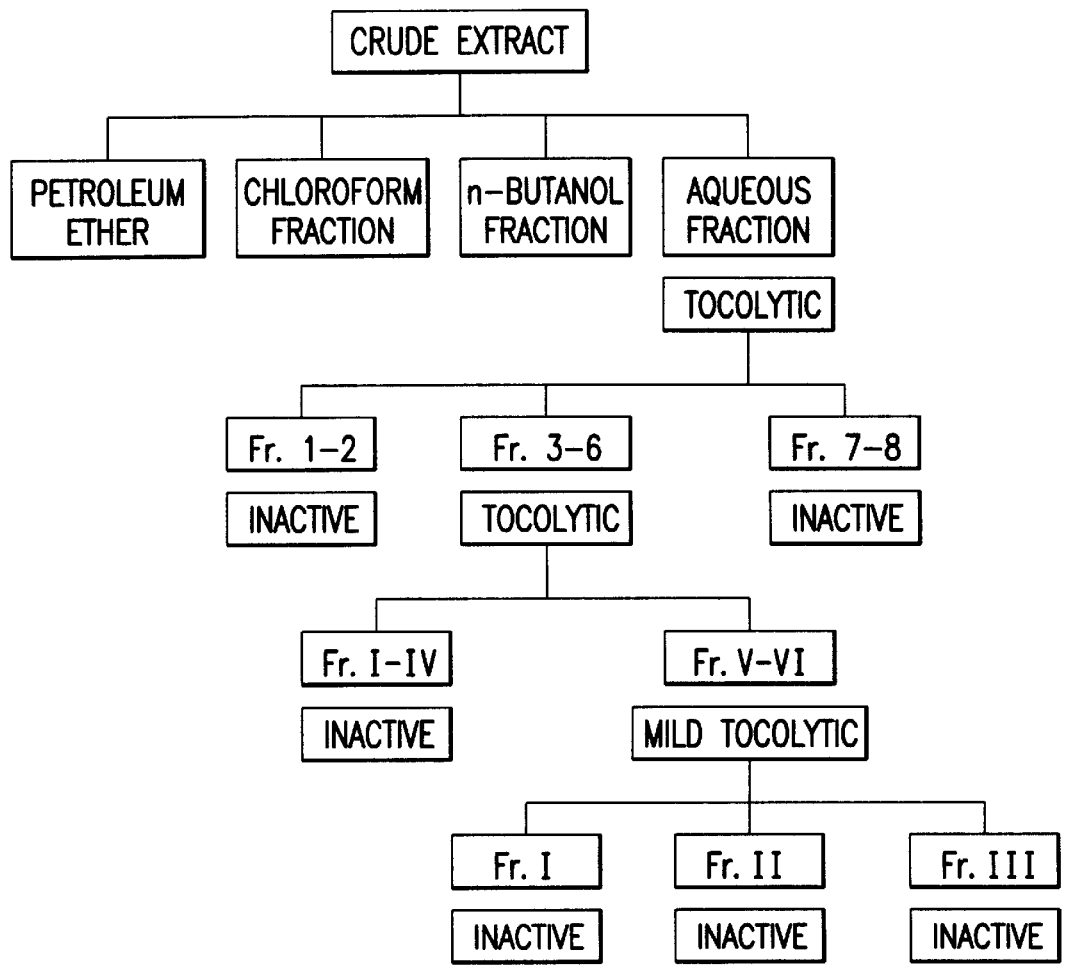

FIG. 8 Fractionation chart of extract of *Salvadora persica*

The invention is described in detail and illustrated by the following examples which should not be construed as limitations on the inventive concept embodied herein.

EXAMPLE 1

This example provides the Chemicals, Reagents, Apparatus used and their sources.

| Name of reagent/chemicals | Company |
| --- | --- |
| Aqueous methanol | Sisco Research Laboratories Pvt Ltd. |
| Petroleum ether | Ranbaxy Fine Chemicals Ltd. |
| Chloroform | Sisco Research Laboratories Pvt Ltd. |
| Butanol | Sisco Research Laboratories Pvt Ltd. |
| Ethyl acetate | Sisco Research Laboratories Pvt Ltd. |
| Histamine acid phosphate | Blenkinsop & Co. Ltd |
| Acetylcholine chloride | Hopkin & Williams Ltd. |
| 5-Hydroxytryptamine creatine sulphate | Sigma Chemicals |
| Barium chloride | Apex Chemicals |
| Nicotine sulphate | BDH chemicals |
| Oxytocin | Parke Davis India Ltd. |
| Prostodin-PGF 2 alpha | Astra IDL Ltd. |

Apparatus
1. Physiograph
   Company: Biodevices,
   Ambala, India.
2. Force Transducer
   Model No. T-305
   Co.: GRASS, USA
3. Stimulator
   Model SS44
   Co. Biodevices, Ambala
4. Polygraph
   Model 7
   Co. GRASS, USA.
5. Force Transducer
   Model No. FT-03
   Co.: GRASS, USA
6. Organ Bath
   Ambala,
   India

EXAMPLE 2

Collection of the mangrove plant *Salvadora persica* L from the coast of Goa, a state in India was along Ribandar, near the mouth of the Mandovi estuary, upstream (India). This species is ubiquitous to the coastal areas of Goa and was collected manually from the intertidal banks.

EXAMPLE 3

Processing of the collected mangroves were washed first with seawater followed by tap water. The undesired materials were sifted out while washing with tap water to get rid of the salts. The leaves, stems, and flowers of the associated mangrove plant were air dried. After drying, the plant material was cut into small pieces and immersed in the solvent 90% aqueous methanol for a week for extraction. Care was taken to ensure that these were properly soaked/dipped in the solvent and checked for putrefaction.

EXAMPLE 4

Extraction and preparation of crude extract was carried out by cold percolation method at room temperature and by solvent evaporation at a water bath (temperature 50° C.)

under reduced pressure. This helps in protection of any heat labile metabolite present in it. Re-extraction was done twice until the extract was concentrated under vacuum to obtain the crude extract.

EXAMPLE 5
Fractionation of the Crude Extract

The crude extract was partitioned into petroleum ether, chloroform, n-butanol and aqueous fractions using a separating funnel. Petroleum ether was added to the extract in the separating funnel and separated out. Next, chloroform was added to the residue, mixed well and the lower layer separated. To the residue butanol was added and the top layer represented the butanol fraction and lower layer the aqueous fraction. Extraction of each fraction was done thrice and whenever there was emulsion sodium chloride was added for breaking the emulsion. Sodium sulphate was added to chloroform and butanol fractions to remove traces of water before concentration. All the fractions were concentrated in the same manner as the crude extract. These fractions were tested for the same pharmacological activity as the parent crude extract. Column chromatography for isolation of pure compound was done by repeated column chromatography and thin layer chromatography of the eluents. The TLC revealed compounds such as Beta-amyrin, betulin, ursolic acid and lupeol.

EXAMPLE 6

To obtain the compounds Beta amyrin and betulin, separation by thin layer chromatography is carried out on 0.25 mm thick silica gel plates (Qualigen). The eluent is an 90:10 (v/v) Petroleum ether/ethyl acetate mixture and the spots are developed by spraying with 5% $H_2SO_4$ solution and fixation by heating at 110.degree. C.

For compounds Ursolic acid and Methyl palmitate separation by thin layer chromatography were carried out on 0.25 mm thick silica gel plates (Qualigen). The eluent is an 85:15 (v/v) Petroleum ether/ethyl acetate mixture and the spots are developed by spraying with a 5%$H_2SO_4$ solution and fixation by heating at 110° C.

For the compound lupeol the separations by thin layer chromatography are carried out on 0.25 mm thick silica gel plates (Qualigen). The eluent is an 75:25 (v/v) Petroleum ether/ethyl acetate mixture and the spots are developed by spraying with a 5% $H_2SO_4$ solution and fixation by heating at 110.degree. C.

In the present invention, the active aqueous fraction of the mangrove plant *S. persica,* was column chromatographed over silica gel for the isolation of the active constituent. Elutes from the column with the same TLC profile were mixed and subjected to pharmacological testing. The active subfractions were further chromatographed till active pure compounds were obtained. Spots on thin layer chromatography (TLC) were visualised by using iodine vapours and spraying with methanolic sulphuric acid. TLC was done on glass plates (20×20 cms) coated with a 0.25 mm layer of TLC grade silica gel (Qualigens) activated at 110° C. for 1 hour before use. The active aqueous fraction was passed through XAD-column and eluents were treated, as mentioned above, for the isolation and purification of active constituent metabolites.

The five compounds were identified on the basis of spectral data obtained at the Regional Sophisticated Instrumentation Centre (RSIC) by the following spectra:

$^1$HNMR for determining the proton environment of the molecule carried out on Bruker DPX-200 MHz.

Apparatus

Bruker Spectrometer

Model: DPX

Co. Bruker $^{13}$CNMR for carbon atoms Bruker DPV 300 MHz.

The compounds were identified from a comparison of their spectral data with those of similar compounds reported in literature.

Mass spectra (EIMS) electron impact Mass spectrometry for determining the molecular weights along with its fragmentation pattern were carried out on Mass spectrometer (El/CIMS) Model D.300 JEOL, Apparatus Mass Spectrometer (EIMS)

Model: D-300

Co. JEOL, Japan

EXAMPLE 6

Pharmacological Testing of Pure Compounds

Standard drugs used were the following:

Histamine acid phosphate (Blenkinsop & Co. Ltd) on ileum.
Acetylcholine chloride (Hopkin & Williams Ltd) on ileum.
5-Hydroxytryptamine creatinine sulphate (sigma Chemicals Co.) on gastrointestinal tract.
Barium chloride (Apex Chemicals) on smooth muscle contraction.
Nicotine sulphate (BDH Chemicals) on intestine as ganglion stimulant.
Oxytocin (Parke Davis India Ltd) on uterus.
Prostodin—$PGF_2$ (Astra IDL Ltd) on uterus.
All other reagents used were of analytical grade.
Tyrode was used on guinea-pig ileum and de Jalon's solution was used on guinea-pig uterus.
Ringer-Locke physiological solution was used on guinea-pig atria table 3.
All other reagents used were of analytical grade.
Physiological solutions used and various parameters:
All physiological solutions were prepared fresh at the time of the experiment.
pH: The pH of the various physiological salt solutions varied between 7.3 & 7.4. At lower pH the tonus of the preparation tends to decrease and is therefore liable to alter the effect of drugs.
Temperature: In order to get consistent effects it was important to maintain the temperature of the bath solution at a specified level, because if the temperature is decreased below 37° C., the tonus of the intestine is increased, the contractions become smaller and the contraction and relaxation times increased.

Air: Air or oxygen is needed for proper functioning of the tissues. Besides, providing oxygen to the tissues, the stream of gas bubbles also stirred the bath solution thereby facilitating diffusion of drugs added to the bath. The solution in the bath was changed frequently because prolonged aeration tends to alter the pH.

In vitro Experiments

Female, virgin, guinea pigs weighing around 300 to 350 g, housed under uniform husbandry conditions (temperature 25±1° C.) were used. The animals were starved 24 hours prior to the experiment, only water was provided ad libitum. The isolated guinea pig uterus was used to study the tocolytic activity.

For experiments upon isolated guinea pig, the bicornuate uterus was dissected out and freed of fat tissue. One horn was cut-off and kept in a shallow dish containing the physiological solution—de Jalon's fluid which was previously aerated with air. Air was preferred to oxygen as the tissue was thin and saturation was faster. Jalon's fluid comprises:

| | |
|---|---|
| Glucose | 0.5 g |
| Sodium chloride | 9.0 g |
| Sodium bicarbonate | 0.5 g |
| Potassium chloride | 0.42 g |
| Calcium chloride | 0.06 g |

All were dissolved in 1000 ml water

The two ends were sutured. The lower end of the uterine strip was tied to a tissue holder and suspended in an organ bath of 10 ml capacity and the upper end being more sensitive, to the lever of the force transducer (FT 03) connected to a Grass Polygraph (Model 7). It was left to stabilize for 30 mins, renewing the physiological solution in the bath every 10 mins. The response of the uterus to different doses of the extract (50 & 250 µg/ml) against standard uterine stimulants like oxytocin and PG $F_{2\alpha}$ with a contact period of 60 seconds (was recorded on the polygraph). The tocolytic effect was evaluated by the following formula:

$$\% \text{ Inhibition} = \frac{X - Y}{X} \times 100$$

Wherein

X=Height of standard contraction (mm)

Y=Height of standard contraction in presence of the extract (mm)

The relative in vitro tocolytic effect of *Salvadora persica* crude extract on guinea pig uterus is shown in the Table hereinbelow (mean of 5 readings):

| EXTRACT | TISSUE | SPASMOGENS | STANDARD INDUCED CONTRACTION (mm) | DOSE 50 mg/ml (mm) | INHIBITION % DECREASE | DOSE 250 mg/ml | INHIBITION % DECREASE |
|---|---|---|---|---|---|---|---|
| Crude Extract | Guinea-pig Uterus | Oxy & PG | 48 | 25 | 48 | 20 | 58 |
| Chloroform | | Oxy & PG | 50 | 50 | 0 | 50 | 0 |
| BuOH | | Oxy & PG | 51 | 48 | 6 | 40 | 21 |
| Aqueous | | Oxy & PG | 48 | 35 | 27 | 25 | 48 |
| Fraction-1 | | Oxy & PG | 45 | 44 | 2 | 42 | 7 |
| Fraction-2 | | Oxy & PG | 48 | 48 | 0 | 45 | 6 |
| Fraction-3 | | Oxy & PG | 50 | 42 | 16 | 30 | 40 |
| Fraction-4 | | Oxy & PG | 50 | 44 | 12 | 28 | 44 |
| Fraction-5 | | Oxy & PG | 46 | 40 | 13 | 26 | 43 |
| Fraction-6 | | Oxy & PG | 48 | 40 | 17 | 24 | 50 |
| S. fr I | | Oxy & PG | 49 | 52 | — | 52 | + |
| S. fr II | | Oxy & PG | 50 | 50 | 0 | 52 | + |
| S. fr III | | Oxy & PG | 48 | 40 | 20 | 32 | 40 |
| S. fr IV | | Oxy & PG | 50 | 45 | 10 | 33 | 34 |
| S. fr V | | Oxy & PG | 50 | 48 | 4 | 45 | 10 |
| S. fr VI | | Oxy & PG | 52 | 50 | 4 | 50 | 4 |

Potentiation
Abbreviations used:
OXY = Oxytocin; PG = PGF 2α

What is claimed is:

1. A method of relieving pain in the uterine muscles, said method comprising administering a therapeutically effective amount of an aqueous extract obtained from a crude extract of the plant *Salvadora persica*, optionally with conventional additives to a subject in need thereof.

2. A method as claimed in claim 1, wherein the crude extract is obtained by cold percolation of material from the plant *Salvadora persica*.

3. A method as claimed in claim 1, wherein the amount of the aqueous extract administered to the subject for a period of 10 minutes ranges between 50 and 250 µg/ml.

4. A method as claimed in claim 1, wherein the subject is a human or an animal.

5. A method as claimed in claim 1, wherein the crude extract is obtained from the stem, leaves and flowers of the plant *Salvadora persica*.

6. A method as claimed in claim 1, wherein the crude extract is obtained from at least one selected from the group consisting of the stem, leaves and flowers of the plant *Salvadora persica*.

* * * * *